United States Patent [19]

Kihara et al.

[11] Patent Number: 4,459,842
[45] Date of Patent: Jul. 17, 1984

[54] ROLL WEAR TESTING METHOD AND APPARATUS THEREFOR

[76] Inventors: Junji Kihara, 5-5-3, Matsubara, Setagaya-ku, Tokyo; Keiji Watabe, 2-11-7, Midorigaoka, Atsugi; Kouichi Douya, 590-100, Ouzenji, Tama-ku, Kawasaki; Kazumoto Nakamura, 3-37-34, Sakuragaoka, Setagaya-ku, Tokyo; Shouzo Takeuchi, 4-28-15, Nishishinkoiwa, Katsushika-ku, Tokyo, all of Japan

[21] Appl. No.: 319,721

[22] Filed: Nov. 9, 1981

[30] Foreign Application Priority Data

Nov. 12, 1980 [JP] Japan .................................. 55/158142

[51] Int. Cl.³ .......................... B21C 51/00; B21B 37/12
[52] U.S. Cl. .................................................. 73/7; 72/17; 73/159
[58] Field of Search .......................... 73/7, 9; 116/208; 72/17

[56] References Cited

U.S. PATENT DOCUMENTS

| | | | |
|---|---|---|---|
| 2,373,115 | 4/1945 | Graves | 73/7 |
| 2,457,276 | 12/1948 | Ross | 73/7 |
| 2,519,551 | 8/1950 | Cross et al. | 73/7 |
| 4,356,714 | 11/1982 | Quehen | 73/159 |

OTHER PUBLICATIONS

Publ. "Wear Testing Machine", by EA Pamfilov. Ind. Lab, (U.S.A.), vol. 37, No. 5, (May 1971), pp. 793-794.

Primary Examiner—Daniel M. Yasich
Attorney, Agent, or Firm—Oldham, Oldham, Hudak, Weber & Sand Co.

[57] ABSTRACT

The present invention relates to an apparatus suitable for accomplishing a roll testing method. The object of the present invention is accomplished by hot rolling steel strip under the specified rolling condition using small size testing apparatus having about a tenth size of the actual rolling mill and good reciprocity like said rolling mill. The wear state (roughness), or new state, of the roll surface is estimated by a known type of surface roughness meter from the roll surface generated after hot-rolling the stell strip by the small size testing apparatus of the present invention. Said testing apparatus has the structure in which both the diameter of the rolls and the circumferential speed of the rolls are about a tenth of those of actual rolling mill and the number of the contact times (contact interval) between the rolls and the stell strip per the rolling time is the same to that of the actual rolling mill.

2 Claims, 4 Drawing Figures

ROLL WEAR TESTING METHOD AND APPARATUS THEREFOR

BACKGROUND OF THE INVENTION

The present invention relates to a roll wear testing method and an apparatus suitable for accomplishing said method.

In more detailed, the present invention relates to the roll wear testing method using the small size testing apparatus having about a tenth size of the actual rolling mill which is practically used.

In the past, it has been attempted to carry out the wear test of roll by the small size testing apparatus.

However, the small size testing apparatus having the good reciprocity like the actual rolling mill could not be developed and accomplished.

Therefore, heretofore, the rolling type wear testing apparatus usable at the high temperature has been used as the most reliable roll wear testing apparatus (referred to MUTA et al. TETSU TO HAGANE '74-S148.60 No. 4 Mar. 1974 ).

However, the wear state or roughness of the roll surface after hot-rolling the steel strip by the actual rolling mill could not be fully reappeared by the small size testing apparatus which has been ordinarily used for the estimation of the roughness of roll surface.

As the result of research and development carried out by the inventors of the present invention, the small size roll wear testing apparatus which has about a tenth size of the actual rolling mill and the roughness of roll surface generated after hot-rolling the steel strip by the actual rolling mill, and the roll wear testing method using the apparatus as mentioned above have been accomplished.

SUMMARY OF THE INVENTON

The present invention lies in providing a roll wear testing method of hot-rolling steel strip, having less than 1 mm (0.39 inch) in thickness and less than 30 mm, (11.7 inch), preferably 15–20 mm (5.85-7.8 inch), in width under the maximum roll force of 6,000 kgf (kgf=9.80665N, 1N=kgm/sec$^2$) at the temperature from the room temperature to 1,200° C, and at the maximum rolling speed of 200 m per minute with the maximum rolling reduction of 40%, using the small size roll wear testing apparatus in which both the diameter of roll and the circumferential speed of roll are reduced to about tenth those of the practical rolling mill, and the number of the contact times (contact interval) between the roll and the steel strip per the rolling time is adjusted so as to be the same to that of the actual rolling mill.

The apparatus of the present invention makes it possible to accomplish the object of the present invention that the roughness of roll surface generated after hot-rolling the steel strip by the actual rolling mill is fully reappeared by the roll wear testing apparatus of the present invention.

BRIEF DESCRIPTION OF THE DRAWINGS

In FIG. 2, the axis of ordinate indicates the profile ($\mu$) of the roll surface, the abscissa indicates the width (mm) of roll.

In FIG. 3, the axis of ordinate indicates the roll profile ($\mu$), the abscissa indicates the width (mm) of roll.

DETAILED DESCRIPTION OF THE INVENTION

Figure 1:
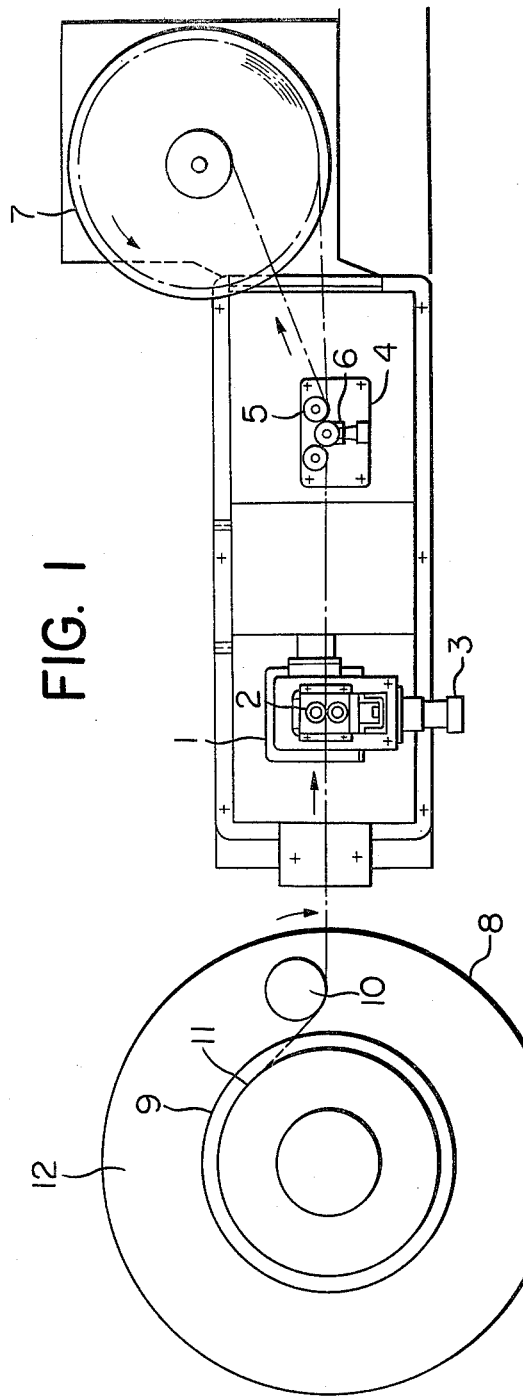
FIG. 1 shows the general view of the roll wear or roughness testing apparatus of the present invention.

The present invention is explained in detail, by the attached drawing FIG. 1 as follows:

One of the apparatus suitable for practicing the method of the present invention comprises the feeding means 12 of the [plating material to be rolled] steel strip, the rolling means 1, the winding up means 7 of said strip, and the conventional means 4 for measuring the forward tension of said [material] strip.

Said feeding means 12 is provided with the winding back means 9 accompanied with the guide roll 10 in the furnace 8 having the maximum heating speed of 80° C. per minute and being installed in the fuel rich atmosphere.

Said rolling means 1 comprises a pair of the conventional rolls 2 which are shaped as vertical rings, and the compression means 3 capable of compressing the material to be rolled under such as a hydraulic jack, which is in conventional use. The maximum roll force is 6,000 kgf.

In said rolling means 1, the distance (or interval) between the outlet of the furnace and the inlet of the rolling mill is shortened to the extend capable of controlling the temperature of the steel strip 11, and both the diameter of roll and the circumferential speed of roll are reduced to about a tenth of those of the actual rolling mill, and the number of the contact times (contact interval) between the roll and the steel strip per the rolling time can be adjusted so as to be the same to that of the actual rolling mill.

In the representative rolling means 1 of the present invention, the diameter of roll is 70 mm, the width of roll is 40 mm, at the circumferential speed of roll is 200 mm per minute at the maximum, and the space between a pair of rolls is less than 1 mm. The roll is made of for example, the material of graphite precipitated structure.

Other material may be used for the roll strip.

Said means 4 for measuring the forward tension of the steel comprises a pair of the guide rolls 5 and, the load cell 6 thereby adjusting the speed of the winding up means 7 so as to be the sme to the speed of the steel strip at the outlet of roll.

As the cooling apparatus of roll, the spray type cooling apparatus of roll.

However, other cooling apparatus may be used.

EXAMPLE

The steel strip was hot-rolled under the following test condition using the roll wear testing apparatus of the present invention (manufactured by DAITO MANUFACTURING CO., Tokyo) as shown in FIG. 1 in order to accomplish the roll wear testing method of the present invention.

The rolling condition was shown as follows:

| | |
|---|---|
| Roll Material: | the material of graphite precipitated structure. |
| Steel Strip: | SPCC (Two pieces of 0.7 mm × 17 mm × 400 mm) |
| Roll Force: | 4,000 kgf |
| Rolling Speed: | (the circumference speed of roll): 180 m/minute |
| Temperature of the steel strip: | 900–950° C. |
| Rolling length: | 800 m |

Cooling system of roll is the system of spraying water under the hydraulic pressure of 11 kg/cm$^2$ by means of the nozzle at the outlet of roll.

TEST RESULT

After hot-rolling the steel strip according to the method of the present invention, the roughness of roll surface (roll profile) was estimated by the surface roughness meter JISBO651, ISO1879, 1880, 3274 (International Organization for Standardization.

Figure 2:
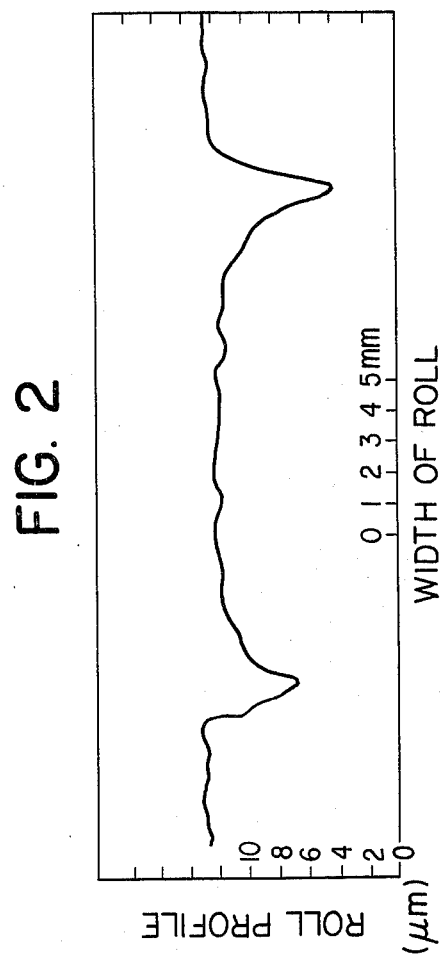
FIG. 2 shows the roughness of the roll surface (roll profile) generated after hot-rolling the steel strip by the roll wear testing apparatus of the present invention.

The test result was shown in FIG. 2.

In order to compare the roughness of the roll surface (roll profile) generated after hot-rolling the steel strip by the actual rolling mill, the roughness of the roll surface (roll profile) generated from both of them was estimated by the surface roughness meter.

The test condition (the rolling condition of the steel strip and the method of estimating the roughness of the roll surface) was substantially same.

Figure 4:
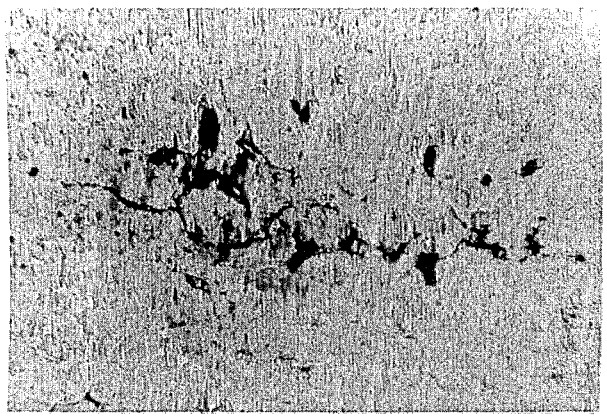
FIG. 4 shows the metallurgical microscopic photograph (magnification) 37.5 times) displaying the roughness of roll surface (roll profile) generated after hot-rolling the steel strip by the testing apparatus of the present invention.

The metallurgical microscopic photograph (magnification of 37.5 times) showing the roughness of the roll surface (roll profile) [obtained] generated after hot-rolling the steel strip by the testing apparatus of the present invention was shown in FIG. 4.

Figure 3:
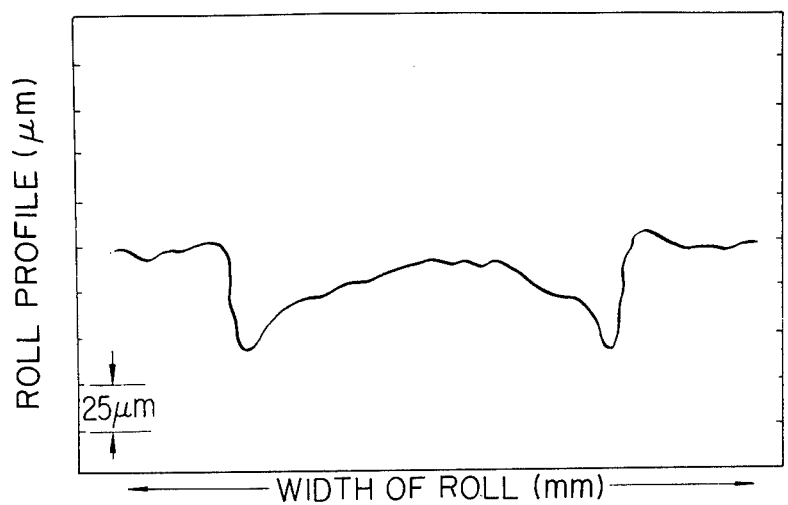
FIG. 3 shows the roughness of the roll surface (roll profile) generated after hot-rolling the steel strip by the rolling mill.

From the roughness of the roll surface as shown in FIGS. 2 and 3, it has been found that the roughness of the roll surface generated after hot-rolling the steel strip by the testing apparatus of the present invention is the same extend to that generated after hot-rolling the steel strip by the actual rolling mill.

Therefore, it has been proved that the roughness of the roll surface generated after hot-rolling the steel strip by the actual rolling mill can be reappeared from the test result generated after hot-rolling the steel strip by the testing apparatus of the present invention.

The characteristic features of the present invention are shown as follows:

(1) The steel strip having less than 1 mm in thickness and less than 30 mm in width can be hot-rolled to the rolling length of about 500 m at the temperature of about 1,000° C. at one test according to the present invention on order to estimate the roughness of the roll surface. And also, the steel strip can be hot-rolled to the rolling length of few thousand meters per day by the apparatus of the present invention.

(2) As both the diameter of roll and the circumferential speed of roll are reduced to about tenth those of the actual rolling mill, the number of the contact times (contact interval) between the roll and the steel strip per the rolling time in the testing apparatus of the present invention can be adjusted so as to be the same to that of the actual rolling mill.

(3) The roll can be easily renewed, the apparatus of the present invention makes it possible to estimate the roughness of the roll surface generated after hot-rolling the steel strip under the various conditions and at each steps which are difficult to carry out in the actual rolling mill.

(4) As the temperature of the steel strip in the testing apparatus can be varied from the room temperature to 1,200° C, the apparatus of the present invention makes it possible to carry out the roll wear test about the various sorts of the roll material and to be applied to the simulator of the actual rolling mill which is simulating actual hot-rolling.

(5) As the testing apparatus of the present invention is useful for the simulator of the actual rolling mill, the method of the present invention can be applied to the research and development of the various sorts of lubricant, especially the lubricant oil usable for the hot-rolling.

What is claimed is:

1. A roll wear testing apparatus characterized in that the apparatus comprises a feeding means for the steel strip, a rolling means, a winding up means, and a means for measuring the forward tension of the steel strip, the feeding means being provided with a winding-back means accompanied with a guide roll in a furnace having the maximum heating speed of 80° C. per minute and being installed in a fuel rich atmosphere, the rolling means comprising a compression means having a maximum compression force of 6,000 kgf and a pair of vertical ring rolls, the distance (or interval) between the outlet of the furnace and the inlet of the rolling means being short to control the temperature of the steel strip, and both the diameter of the roll and the circumferential speed of the ring rolls being reduced to about a tenth of those of the actual rolling mill, the means for measuring the forward tension comprising a pair of guide rolls and a load cell to adjust the speed of the winding up means to be the same as the speed of the steel strip at the outlet of the rolling means.

2. The roll wear testing apparatus as claimed in claim 1, wherein the diameter of roll is 70 mm, the width of roll is 40 mm, the space between a pair of rolls is less than 1 mm, and the circumferential speed of roll is 200 m per minute at the maximum.

* * * * *